United States Patent
Drexl et al.

(10) Patent No.: US 12,076,093 B2
(45) Date of Patent: Sep. 3, 2024

(54) METHOD OF CALIBRATING A SPINAL CAGE

(71) Applicant: Brainlab AG, Munich (DE)

(72) Inventors: Thomas Drexl, Munich (DE); Dimitrij Surmeli, Munich (DE); Amar Husejic, Munich (DE)

(73) Assignee: BRAINLAB AG, Munich (DE)

( * ) Notice: Subject to any disclaimer, the term of this patent is extended or adjusted under 35 U.S.C. 154(b) by 359 days.

(21) Appl. No.: 17/599,156

(22) PCT Filed: Sep. 30, 2020

(86) PCT No.: PCT/EP2020/077327
§ 371 (c)(1),
(2) Date: Sep. 28, 2021

(87) PCT Pub. No.: WO2022/069028
PCT Pub. Date: Apr. 7, 2022

(65) Prior Publication Data
US 2022/0304753 A1    Sep. 29, 2022

(51) Int. Cl.
*A61B 34/20* (2016.01)
*A61B 34/10* (2016.01)
*A61F 2/44* (2006.01)
*A61F 2/46* (2006.01)

(52) U.S. Cl.
CPC ............. *A61B 34/20* (2016.02); *A61B 34/10* (2016.02); *A61F 2/4657* (2013.01); *A61B 2034/102* (2016.02); *A61B 2034/2055* (2016.02); *A61B 2034/2068* (2016.02); *A61F 2/447* (2013.01);
(Continued)

(58) Field of Classification Search
CPC ............................................... A61B 2034/102
See application file for complete search history.

(56) References Cited

U.S. PATENT DOCUMENTS

| 6,351,659 B1 | 2/2002 | Vilsmeier |
| 2005/0222793 A1 | 10/2005 | Lloyd et al. |

(Continued)

FOREIGN PATENT DOCUMENTS

| EP | 0978258 | 2/2000 |
| EP | 1369090 | 12/2003 |

(Continued)

OTHER PUBLICATIONS

International Preliminary Report on Patentability issued in Application No. PCT/EP2020/077327, 11 pages, dated Apr. 13, 2023.
(Continued)

*Primary Examiner* — Joel Lamprecht
*Assistant Examiner* — Ashish S Jasani
(74) *Attorney, Agent, or Firm* — Gray Ice Higdon

(57) ABSTRACT

A computer implemented medical method of calibrating a cage is presented. In particular, this calibration method calculates a virtual model of the cage based on a cage tip point and a cage end point, acquired by using a pointer tip of a pointing device, and at least one axis, acquired by using a pointer shaft of the pointing device along a side of the cage. This method allows for providing a more detailed virtual model of the cage, while being in compliance with sterility restrictions.

25 Claims, 6 Drawing Sheets

(52) U.S. Cl.
CPC .......... *A61F 2002/4658* (2013.01); *A61F 2002/4663* (2013.01)

(56) References Cited

U.S. PATENT DOCUMENTS

| | | | | |
|---|---|---|---|---|
| 2006/0287613 | A1* | 12/2006 | Amiot | A61F 2/4657 600/587 |
| 2007/0038059 | A1* | 2/2007 | Sheffer | A61B 90/36 600/407 |
| 2011/0251835 | A1 | 10/2011 | Amiot et al. | |
| 2011/0251836 | A1 | 10/2011 | Wang et al. | |
| 2013/0079678 | A1 | 3/2013 | Stein et al. | |
| 2014/0155735 | A1 | 6/2014 | Greer et al. | |
| 2018/0333207 | A1* | 11/2018 | Moctezuma De la Barrera | A61B 34/25 |
| 2020/0405395 | A1* | 12/2020 | Gullotti | A61B 17/7082 |

FOREIGN PATENT DOCUMENTS

| | | |
|---|---|---|
| EP | 1413257 | 4/2004 |
| EP | 1413258 | 4/2004 |
| EP | 1449485 | 8/2004 |
| EP | 3646809 | 5/2020 |
| WO | 9710776 | 3/1997 |
| WO | 0053077 | 9/2000 |
| WO | 2006060107 | 6/2006 |
| WO | 2018189725 | 10/2018 |
| WO | 2022069510 A1 | 4/2022 |

OTHER PUBLICATIONS

International Search Report and Written Opinion issued for Application No. PCT/EP2020/077327 dated Jun. 11, 2021.
European Patent Office, International Search Report and Written Opinion for PCT Patent Application PCT/EP2021/076731 dated Dec. 20, 2021; 16 pages.
European Patent Office, Examination Report for European Patent Application 20788726.6 dated Dec. 14, 2021; 3 pages.
European Patent Office, Examination Report for European Patent Application 20788726.6 dated May 20, 2022; 6 pages.
Tanak M, Ruparel S, Fujiwara Y, Uotani K, Yamauchi T, Simultaneous Oblique Lumbar Interbody Fusion (OLIF) and Lateral Percutaneous Pedicle Screw Fixation (Lateral PPS): A Technical Note, Crimson Publishers, published Feb. 4, 2019, 8 pages.
Ralph J. Mobbs, Kevin Phan, Greg Malham, Kevn Seex, Prashanth J. Rao, Lumbar Interbody Fusion: Techniques, Indications and Comparison of Interbody Fusion Options including PLIF, TLIF, MI-TLIF, OLIF/ATP, LLIP and ALIF, published Dec. 2015, Journal of Spine Surgery, vol. 1, No. 1; 18 pages.
"Interbody devices" Stryker. Retrieved from https://www.stryker.com/us/en/portfolios/orthopaedics/spine-ortho-/interbody-devices.html, 8 pages, dated Nov. 2018.
International Preliminary Report on Patentability issued in Application No. PCT/EP2021/076731, 10 pages, dated Apr. 13, 2023.

* cited by examiner

METHOD OF CALIBRATING A SPINAL CAGE

FIELD OF THE INVENTION

The present invention relates to a computer-implemented method for calibrating a cage, a cage calibration system, a surgical navigation system for computer assisted surgery as well as a computer program.

TECHNICAL BACKGROUND

Cage calibration and navigation aims at facilitating the cage placement workflow like anterior lumbar interbody fusion, ALIF, posterior lumbar interbody fusion, PLIF, transformational lumbar interbody fusion, TLIF, and lateral lumbar interbody fusion, LLIF, procedures and it aims at reducing the amount of radiation exposure to patient and OR staff. While integrated solutions, where the exact cage shape and the cage inserter are known to the software, only need a selection and verification mechanism, or in rare cases their calibration has to be updated by minimal user input, a generic approach to calibrated cages leaves a lot of options in how users can provide input to the software in order to calibrate not only the tip or a front point of the cage, but ideally show a cage shape that resembles the real cage implant.

Calibration devices, like the calibration matrix ICM4 of Brainlab, have early been advised against by experts considering sterility. Furthermore, the calibration devices would need special openings, where the cage can be placed from two sides to show its dimensions, otherwise they do not allow stable cage placement. Additionally the length of the cage can't be easily measured by holding the cage to a calibration device surface.

The present invention can be used for calibration procedures e.g. in connection with a system for image-guided surgery such as in Spine & Trauma navigation.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the light of the prior art descripted hereinbefore, it may be seen as the object of the present invention to provide an improved method for calibrating a cage.

In the following, a short description of the specific features of the present invention is given which shall not be understood to limit the invention only to the features or a combination of the features described in this section.

A computer implemented medical method of calibrating a cage is presented.

In particular, this calibration method calculates a virtual model of the cage based on a cage tip point and a cage end point, acquired by using a pointer tip of a pointing device, and at least one axis, acquired by using a pointer shaft of the pointing device along a side of the cage. This method allows for providing a more detailed virtual model of the cage, while being in compliance with sterility restrictions.

GENERAL DESCRIPTION OF THE INVENTION

In this section, a description of the general features of the present invention is given for example by referring to possible embodiments of the invention.

This is achieved by the subject-matter of the independent claims, wherein further embodiments are incorporated in the dependent claims and the following description.

The described embodiments similarly pertain to the computer-implemented medical method of estimating a position of a medical instrument tip, the use of the estimated position of the instrument tip, the instrument calibration system, the surgical navigation system for computer assisted surgery and the computer program. Synergetic effects may arise from different combinations of the embodiments although they might not be described in detail hereinafter. Furthermore, it shall be noted that all embodiments of the present invention concerning a method, might be carried out with the order of the steps as explicitly described herein. Nevertheless, this has not to be the only and essential order of the steps of the method. The herein presented methods can be carried out with another order of the disclosed steps without departing from the respective method embodiment, unless explicitly mentioned to the contrary hereinafter.

Technical terms are used by their common sense. If a specific meaning is conveyed to certain terms, definitions of terms will be given in the following in the context of which the terms are used.

According to the present disclosure, a computer implemented medical method of calibrating a cage is provided. The method comprises the steps of acquiring, by using a pointer tip of a pointing device, a cage tip point at a cage tip of the cage, wherein the cage tip is disposed at a first end of the cage in a length direction of the cage. Furthermore, the method comprises the step of acquiring, by using the pointer tip of the pointing device, a cage end point at a cage end of the cage, wherein the cage end is disposed at a second end of the cage, opposing to the first end, in the length direction. The method further comprises the step of acquiring, by using a pointer shaft of the pointing device, at least one axis along a side of the cage. Further, the method comprises the step of determining a calibrated virtual model of the cage using the cage tip point, the cage end point and the at least one cage axis.

In other words, the method allows for cage calibration using a pointing device, thereby also determining a virtual model of the cage. The virtual model of the cage is preferably displayed to a user for medical navigation.

The term "pointing device", as used herein, refers to any instrument that has a tip, typically a pointed tip, and is known to the navigation system (by position and orientation) taking into account that sterility and accuracy is sufficient for calibration. The pointing device also comprises a plurality of different instruments, in particular one instrument, which is configured for acquiring points, for example the cage tip point and the cage end point, and another instrument, which is configured for acquiring the axes.

The term "pointer shaft", as used herein, relates to the part of the pointing device, extending away from the pointer tip. In general, a pointing device comprises a pointer handle for holding the pointing device and a pointer tip for point acquisition. The pointer handle and the pointer tip are connected over the pointer shaft.

The term "cage", as used herein, also is referred to as "spinal cage", being an implant. The cage is usually inserted into the spine of a patient during a procedure called spinal fusion, wherein the space between two discs is filled with the cage and bone-growth promoting material. In general, the term cage describes cages as known from interbody fusion procedures. Furthermore, the term cage also refers to artificial discs or any other cage-shaped implants that are inserted to replace the intervertebral disc, or parts of the disc like the nucleus, as all these cage-like implants can be calibrated by the given method.

The terms "cage end" and "cage tip", as used herein, describe two points of the cage at opposing sides of the cage. Usually, the cage comprises an elongated shape, wherein the cage end and the cage tip are consequently defined at the ends of the elongated sides of the cage. Preferably, the cage end and the cage tip are disposed at opposing sides of the cage, wherein the distance between the cage end and the cage tip has a maximal possible value. If the cage end and/or the cage tip are disposed at a flat side, the cage end and/or the cage tip are defined as being in the centre of the flat side.

As the usual cage comprises an elongated shape, the length direction is defined along this elongation, while the width direction is defined perpendicular to the length direction. If the cage comprises a square shape, in other words, the cage is as wide as long, one direction is just defined as length direction and the other directions are defined based on this definition.

The term "virtual model", as used herein, comprises a digital representation of the cage.

The term "axis", as used herein, comprises a digital line that indicates the position and orientation of the pointing device when acquiring the axis. The axis thus allows for approximation of a side of the cage.

Acquiring the cage tip point and the cage end point allows for displaying the cage as a virtual line. Acquiring at least one axis along a side of the cage allows, together with the already acquired cage tip point and the cage end point, to determine a shape of the cage.

Due to sterility restrictions, the pointer shaft is not moved along the sides of the cage, but single axis are acquired. For sterility reasons, also as few measurements as possible should be executed and thus as few as possible axis should be acquired. For a symmetric cage, an amount of two axis and for an asymmetric cage, an amount of four axis is preferred. The information, if the shape of the cage is symmetric can be provided by a user. Preferably, if only two axis are acquired, it can be determined based on that the cage is symmetric and the other two axis are determined by symmetry calculations.

Preferably, the method comprises the step of indicating to a user an acquisition position, where on the cage, in other words on which side of the cage, the cage tip point, cage end point and/or at least one axis should be acquired by holding the pointing device to the cage. Further preferably, in a previous step, a generic shape of the cage is provided by the user, based on which the indication of acquisition positions is indicated.

The method is preferably used in a navigation system, in particular for computer-assisted surgery. The navigation system tracks objects that can then be displayed to a user of the navigation system. In general, the navigation system comprises a pointing device, wherein the shape of the pointing device is known and the position and/or orientation of the pointing device is known due to markers disposed on the pointing device. The navigation system also comprises a tracking system, in particular a camera, which is configured for tracking the markers. Thus, the navigation system is aware of the shape, position and orientation of the pointing device. The same applies to the holding device of the cage. However, the navigation system is initially not aware of the shape, position and orientation of a cage, held by the holding device. Thus, the cage has to be calibrated. In other words, a spatial relation between the cage and the pointing device is determined. When the cage is calibrated, the navigation system is able to track the cage and consequently can display the cage to the user of the navigation system.

For determining the virtual model of the cage that can be displayed to the user, in particular during navigation, a bounding box of the cage is defined. The bounding box is preferably determined using the cage tip point, the cage end point and the at least one cage axis. Based on this information, an approximation of the shape of the cage in form of a virtual model is determined, allowing for calibration of generic cages, whose shapes are not known.

During cage calibration, the points and at least one axis are acquired step by step. Thus, the virtual model is preferably determined step by step, too. In other words, the virtual model is determined using the cage tip point, the cage end point and one axis. If the user is already satisfied with the representation of the cage that the virtual model provides, the user can finish the calibration method. Otherwise, more axes are acquired for determining a more fitting representation of the cage.

Preferably, the user is guided through the calibration method, by indicating which point or axis needs to be measured, or in other words approximately where the user has to put the pointing device in view of the cage, for example by a graphic animation. For example, the user is requested to put the pointer tip on the cage end and the cage tip or to put the pointer shaft on a side of the cage.

Thus, the method allows calibrating a cage of any generic shape, in particular for different medical procedures.

Thus, the method allows calibrating a cage meeting sterility restrictions, in particular allowing sensitive materials of the cage or sensitive coatings of the cage.

Consequently, an improved method of calibrating a cage is provided.

In the following preferred embodiments will be described in more detail.

According to another exemplary embodiment of the present invention, acquiring the cage end point, the cage tip point and/or the at least one cage axis comprises determining a cage-to-holder-coordinate-transformation, which describes a transformation between a holder coordinate system of the holding device and a cage coordinate system of the cage.

Preferably, the pointing device and the holding device comprise markers that can be tracked by a tracking device. The tracking device preferably comprises two cameras to track markers in 3D space, in particular passive markers. Therefore, a transformation between a coordinate system of the tracking device and a coordinate system of an instrument marker, in this case a holding device marker, is determined. In order to calibrate a holding device with such an attached marker, or in other words marker array, another transformation to the holder coordinate system has to be determined. It has to be noted that introduction of coordinate systems is not a necessity as all calculations can be performed in one world coordinate system, but local coordinate systems add meaning to the local parts that are involved in the calibration and navigation of instruments and thus facilitate calculations using local coordinates. So, instead of memorizing spatial positions including orientations of specific points, all descriptions will as follows use local coordinate systems and calculate transformations between the coordinate systems. Such transformations can be given as matrices, so matrix multiplications transform points into different coordinate systems. The transformation from one system to another is determined by a technique called change of basis, writing the axes into the columns of the transformation matrix that for instance describes the rotation of the cage coordinate system to the holder coordinate system:

CageToHolder=(CageXAxisInHolderCoords,CageYAxisInHolderCoords,CageZAxisInHolderCoords)

In general, this technique is extended to homogenous coordinates using 4×4 matrices to be capable of describing affine transformations, thus CageToHolder can include both, translation and rotation.

In other words, the cage-to-holder-coordinate-transformation describes a transformation of the cage coordinates in X-direction, Y-direction and Z-direction into holder coordinates in X-direction, Y-direction and Z-direction.

This transformation is called the calibration or calibration transformation or calibration matrix of a cage that is rigidly attached to the holding device.

As the tracking device is only capable of identifying marker positions, in order to calibrate a holder device holding a cage, a tracked calibration device is necessary, so the user holds the cage tip with unknown position against a known point on the calibration device. Thus, the cage tip position becomes known. As no usual calibration device, as for example the Brainlab ICM4, is suitable for the described cage, the calibration device used herein is actually another instrument, a so called pointing device. The shape, orientation and position of the pointing device are known to the tracking device. Consequently, when holding the pointer top of the pointing device against the cage tip of the cage, the position of the cage tip becomes known to the tracking device.

Consequently, an improved method of calibrating a cage is provided.

According to another exemplary embodiment of the present invention, acquiring the cage end point, the cage tip point and/or the at least one axis comprises providing a pointer-to-holder-coordinate-transformation, PointerToHolder, which describes a transformation between the pointer coordinate system, Pointer, and the holder coordinate system, Holder, and determining the holder-to-cage-coordinate-transformation, HolderToCage, by using the pointer-to-holder-coordinate-transformation, PointerToHolder.

In order to determine the cage-to-holder-coordinate-transformation, CageToHolder, a relationship between the cage coordinate system and the pointer coordinate system, in other words the cage-to-pointer-coordinate-transformation, CageToPointer, is determined by using the pointing device. A relationship between the pointer coordinate system and the holder coordinate system, in other words the pointer-to-holder-coordinate transformation, PointerToHolder, is known due to the disposed markers. Thus, the cage-to-holder-coordinate-transformation, CageToHolder, can directly be calculated from CageToPointer concatenated with PointerToHolder, in particular by equation 1.

CageToHolder=CageToPointer*PointerToHolder   (1)

Consequently, an improved method of calibrating a cage is provided.

According to another exemplary embodiment of the present invention, acquiring the cage end point, the cage tip point and/or the at least one axis comprises holding the pointing device onto the cage until the respective cage end point, cage tip point and/or at least one axis is acquired.

Preferably, acquiring a point or an axis comprises determining a spatial position of the point or axis. Further preferably, acquiring a point or position comprises determining a plurality of spatial positions of the point or axis over a predetermined amount of time, determining a standard deviation of the plurality of spatial positions and accepting an acquired point or axis, when the standard deviation is lower than a predetermined threshold. Consequently, when the standard deviation is bigger than the predetermined threshold, the acquired points or axis are discarded.

Preferably, a signal is provided to the user, when a point, in particular cage end point or cage tip point, or an axis is acquired.

Acquiring a point or an axis requires a minimum time span, where the pointer tip or the pointer shaft are held still. It is then assumed that the pointing device is held against an object that is being calibrated. Consequently, holding the pointing device in the air can be differentiated from holding the pointer against the object to be calibrated. The standard deviation of spatial positions of the pointer device is much smaller when held still against an object to be tracked compared to holding the pointing device in the air. Consequently, acquiring a point or axis comprises collecting spatial positions of the pointer tip and/or the pointer shaft over time and giving the standard deviation of the positions as a result.

Preferably, acquiring a point or axis comprises collecting a spatial position of the pointing device, in particular the pointer tip and/or the pointer shaft. Further preferably, a plurality of spatial positions of the pointing device are collected over time. The pointer tips and shafts, in form of 3D shaft points, each are memorized in a list that is suitable for evaluating statistical properties like the standard deviation. Based on time stamps, the actual used pointer tips within the desired time interval stay in the list, everything older is removed. Therefore, the time stamps are memorized in a cyclic list that is capable of storing the maximum available time stamps over the given time, which is (MaxFPS*acquisitionMilliseconds/1000), independent from the current frame rate of the system. The current index of the list is memorized, so the correspondence to entries of the point list is given. When a new pointer tip point or shaft point is available, it is stored in the tip/shaft list, the current time stamp is stored and the length of the tip/shaft list is updated according to the time stamps.

According to another exemplary embodiment of the present invention, the virtual model indicates a shape, position and orientation of the cage.

Preferably, the virtual model represents the shape of the cage. Furthermore, as the different points and/or axis of the virtual model are stored in cage coordinates and the different coordinate transformations are known, also the position and orientation of the cage in the 3D space is known.

According to another exemplary embodiment of the present invention, the virtual model comprises a multi-dimensional representation of the cage, in particular a 3-dimensional representation of the cage.

In the most simple form, a 2-dimensional representation of the cage is provided. However, when taking the cage end point, the cage tip point and at least one axis into account, a bounding box around the known points and axis allow a 3-dimensional representation of the cage.

According to another exemplary embodiment of the present invention, acquiring the cage end point comprises the step of acquiring a first holder point and a second holder point at opposing lateral sides of a cage holder, which holds the cage at the second end of the cage, by using the pointer tip of the pointing device. The method further comprises the step of determining the cage end point as a centre of a connection line between the first holder point and the second holder point.

Preferably, the acquired cage tip point and the acquired cage end point are discarded if they do not comply to predetermined restrictions. The restrictions allow discarding presumably wrongly acquired points. For example, a distance between the cage tip point and the first holder point, as well as a distance between the cage tip point and the second holder point must be at least a predetermined value, like 10 mm. Further, for example, a distance between the first holder point and the second holder point must be at least a predetermined value, like 3 mm. Those restrictions allow discarding acquired points that cannot fit to known cage designs. In other words, the acquired cage tip point and/or the acquired cage end point is discarded, if they do not comply to predetermined restrictions using a distance between the cage tip point and the second holder point and/or a distance between the first holder point and the second holder point.

Preferably, if the restrictions are fulfilled, a corresponding signal is provided, for example, a sound is played, and the acquired point is stored, in particular in holder coordinates, accordingly.

According to another exemplary embodiment of the present invention, the method comprises the step of acquiring, by using the pointer shaft of the pointing device, at least one axis along at least one lateral side of the cage in a height direction of the cage.

As the cage tip point and the cage end point are already known, a length of the cage can be approximated. In order to extend the virtual model of the cage, information about a width of the cage would be useful. This can be achieved by determining at least one axis along at least one lateral side of the cage in the height direction of the cage. Each axis along a lateral side of the cage in the height direction provides information about an extension of the cage in a width direction.

This allows for a more detailed approximation of the shape of the cape, improving the calibration of the cage.

According to another exemplary embodiment of the present invention, the method comprises the step of acquiring, by using the pointer shaft of the pointing device, at least one axis along a top side and/or bottom side of the cage in a width direction of the cage.

Each axis along a top side and/or bottom side of the cage in the width direction provides information about an extension of the cage in a height direction.

This allows for a more detailed approximation of the shape of the cape, improving the calibration of the cage.

According to another exemplary embodiment of the present invention, the method comprises the stop of acquiring, by using the pointer shaft of the pointing device, at least one axis along a top side and/or bottom side of the cage in a length direction of the cage.

Based on the general shapes of various cages, a measurement of an axis along the top side and/or bottom side of the cage in a width direction provides the most profitable additional information, as the cage tip point and the cage end point already provide information of the cage along the length direction and the axis along the lateral sides of the cage provide information of the cage along the height direction.

In some cases, instead of acquiring the fourth axis along the top side of the cage in the width direction, an acquisition of the fifth axis along the top side of the cage in the length direction provides more insights about the cage of the shape. For example, if the cage comprises a top side, which is inclined in a length direction, a fifth axis along the top side of the cage in the length direction provides more information about the shape of the cage than the fourth axis along the top side of the cage in the width direction. For sterility reasons, as few measurements as possible should be executed and thus as little as possible axis should be acquired.

For example, if a shape of the cage comprises a lordotic shape with an inclined surface in the length direction of the cage, instead of acquiring at least one axis along the top side and/or the bottom side in the width direction, the at least one axis is acquired along the top side and/or bottom side in the length direction. Thus, the inclined surface in the length direction of the cage, in particular a lordotic angle, defining the amount of inclination of the inclined surface, can be measured.

This allows for a more detailed approximation of the shape of the cape, improving the calibration of the cage.

According to another exemplary embodiment of the present invention, the method comprises the following steps: Acquiring, by using the pointer shaft of the pointing device, a first axis long a first lateral side of the cage in a height direction of the cage, a second axis along a second lateral side of the cage opposite of the first lateral side, in the height direction of the cage, a third axis along a top side of the cage in a width direction of the cage, and a fourth axis along a bottom side of the cage in the width direction of the cage.

According to another exemplary embodiment of the present invention, the method comprises the following steps: Acquiring, by using the pointer shaft of the pointing device, a first axis along a first lateral side of the cage in a height direction of the cage, a second axis along a second lateral side of the cage opposite of the first lateral side, in the height direction of the cage, a fifth axis along a top side of the cage in a length direction of the cage, and a sixth axis along a bottom side of the cage in the length direction of the cage.

According to another exemplary embodiment of the present invention, for acquiring the at least one axis in the width direction and/or height direction, the pointer shaft is held in a width axis section distant to the cage end point and the cage tip point.

In order to acquire a maximum amount of information of the shape of the cage with a minimum amount of acquired points and/or axis, the at least one axis is acquired distant to the cage end point and the cage tip point, which already provide shape information of this part of the cage.

Thus, it is prevented to acquire redundant information from different acquired points and/or axis.

Preferably, the width axis section is implemented as an axis restriction. Therefore, the acquired axis is projected onto the cage length axis along the shortest distance to the cage length axis in order to determine an axis point, A, on the cage length axis to define the restrictions for the width axis section:

A distance between the axis point and the cage tip point start must be bigger than a quarter of the distance between the cage tip point and the cage end point.

A distance between the axis point and the cage end point must be bigger than a quarter of the distance between the cage endpoint and the cage start point.

The axis point must be between the cage tip point and the cage end point.

In other words, the axis point is somewhere around the centre of the cage, where the dimension of the cage is represented best.

If an acquired axis does not fulfil these requirements, the measurement is discarded.

According to another exemplary embodiment of the present invention, for acquiring the at least one axis in the length direction, the pointer shaft is held in a length axis section distant to the lateral sides of the cage.

Preferably, the length axis section is implemented as an axis restriction. Therefore, the acquired axis is projected onto the cage width axis, which crosses at the centre between the cage start point and the cage end point, along the shortest distance to the cage width axis in order to determine an axis point on the cage width axis to define the restrictions for the length axis section:

The axis point is somewhere around the centre of the cage, where the dimension of the cage is represented best.

If an acquired axis does not fulfil these requirements, the measurement is discarded.

Thus, it is prevented to acquire redundant information from different acquired points and/or axes.

According to another exemplary embodiment of the present invention, determining a calibrated virtual model comprises determining a cage axis of the cage, determining at least one nearest point of the at least one axis, being the nearest point of the at least one axis to the cage axis, and determining the virtual model using the at least one nearest point.

Preferably, determining the virtual model comprises determining a bounding box of the cage using the at least one nearest point, the cage tip point and the cage end point.

Preferably, a minimum x-value, minx, maximum x-value, maxx, minimum y-value, miny, and maximum y-value, maxy, of all the at least one nearest points is determined.

Further, a plurality of approximately parallel lines to the cages x-axis and y-axis with the minimum x-value, maximum x-value, minimum y-value and maximum y-value, or in other words the x-axis and the y-axis of the cage-coordinate system, are determined. If lines are still missing, the cage will be set up symmetrically.

Preferably, symmetric setup is performed by the following steps: If only one axis is parallel to the x-axis of the cage coordinate-system, define the other parallel axis opposite of the defined axis as follows:

If minx<0 then maxx=−minx, but at least 2 mm distance
If maxx>0 then minx=−maxx, but at least 2 mm distance
The same applies for the y-axis.
If no line is parallel to instrument x-axis, then derive x from y and thus define minx=miny and maxx=maxy.
The same applies for the y-axis.

In other words, symmetry is achieved and there are thresholds to prevent creation of an almost infinitely small cage model.

If the shape of the cage has a specific shape, like kidney or lordotic shape that is not covered very well by a cuboid bounding box, such a shape can be defined by a user, for example by a graphic user interface, GUI. In case of a kidney shape, a bending amount can be defined, which is used to adapt the bounding box. In case of lordotic cages, a lordotic angle and a side of the cage having the lordotic shape can be defined by a user, which is used to adapt the bounding box.

According to another exemplary embodiment of the present invention, determining the at least one nearest point comprises the following steps: Determining a length cage axis connecting the cage tip point and the cage end point, determining a width cage axis, extending perpendicular to the length cage axis in the width direction through a centre of the length cage axis in the length direction. Determining at least one nearest point of the at least one axis in the width direction and/or the height direction, being the nearest point of the at least one axis to the length cage axis. Determining at least one nearest point of the at least one axis in the length direction being the nearest point of the at least one axis of the width cage axis.

Thus, the nearest points can be determined for axes in the length direction and for axes in the width or height direction.

According to another exemplary embodiment of the present invention, the method comprises the steps of determining the cage coordinate system in the cage tip point, wherein the cage coordinate system comprises an x-axis, a y-axis and a z-axis, perpendicular to each other, wherein the z-axis is equal to the cage axis, determining at least one projection point, projecting the at least one nearest point into an x-y-plane, defined by the x-axis and the y-axis, determining a distance between the at least one projection point and an at least one planned projection point of a planned axis, wherein the at least one planned axis is a previously acquired axis for the cage, replacing the planned axis with the acquired at least one axis; if the determined distance is smaller than a predetermined threshold, and adding the acquired at least one axis to the previously acquired axis for the cage.

In other words, there is a check, if the newly acquired axis, or in other words current axis, is already available or if one of the previously planned lines needs to be replaced.

The projection point of the newly acquired axis is analysed in view of a projection point of a planned axis. The planned axis thereby indicates an axis that has been previously acquired. Preferably, when acquiring the axes, the already acquired axes for a specific cage are stored for virtual model determination. Those stored already acquired axes are referred to as planned axes.

If a distance between the projection point and the planned projection point is smaller than a predetermined threshold, for example 3 mm, the planned axis is being replaced with the newly acquired axis.

It a distance between the projection point and the planned projection point is bigger than that threshold, the planned axis is not being replaced by the newly acquired axis, but the newly acquired axis is accepted in addition to the planned axis.

If a distance between the projection point and the planned projection point is smaller than another threshold, for example 0.2 mm, and a distance at pointer tip point and at shaft point, marking the end points of an axis, for the newly acquired axis and for the planned axis is also smaller than that threshold, this axis is discarded, because this axis has been already planned before.

For example, the user is not satisfied with the shape of the virtual model because one side is not correctly representing the real shape of the cage. Then the user can measure this specific side again by acquiring the corresponding axis. The described method thus automatically detects that no new axis is acquired, but a previously acquired axis needs to be replaced.

Preferably, determining the calibrated virtual model comprises determining the virtual model using the at least one projection point.

Thus, an improved cage calibration method is provided.

According to another exemplary embodiment of the present invention, replacing the planned axis with the acquired at least one axis comprises the following steps: Determining a replacement likelihood score for each planned axis. Replacing the planned axis with the highest replacement likelihood score with the acquired at least one axis, wherein the replacement likelihood score is determined using a weighted replacement likelihood function, using a distance of the planned axis to the cage axis and a distance of the planned axis to the acquired axis.

If there would be three "approximately parallel" lines, where "approximately parallel" means the angle between both lines is smaller than 45 degree to distinguish from lines form perpendicular cage sides, one of the previously planned lines will be replaced with the line that is most likely to be replaced: therefore a replacement likelihood function is defined for all planned lines that gives a score according to equation 2 for replacement, so the line with the highest score will be replaced.

$$\text{score}=\text{dist}(\text{plannedLine},\text{cageAxis})^w - v^{w-1} \cdot \text{dist}(\text{plannedLine},\text{currentLine})^1 \quad (2)$$

Value w, greater than 1, is used to distribute the weighting: for example w=2 would mean the distance of the planned line to the cage axis does not matter that much near the cage axis, but would be rated as very bad if the planned line is far away from the cage axis, meaning the planned line could be an erroneously placed line and needs to be replaced by the current line. The distribution of the distance between planned line and current line can be left without an exponent (the exponent is 1), because one exponent w is sufficient to create a weighting and because a nearer line becomes proportionally likelier for replacement. Value v is used to scale both scores, thus beyond distance v, the function with exponent has more impact while below distance v, the linear function dominates the result.

Thus, an improved cage calibration method is provided.

According to another exemplary embodiment of the present invention, wherein determining the at least one axis comprises the steps of acquiring at least one shaft point relating to a shaft end distant to the pointer tip and at least one pointer tip point, and determining the at least one axis by connecting the at least one shaft point and the at least one pointer tip point.

For efficiency reasons, each axis is only acquired as a plurality of points. In the simplest form, an axis is defined by the shaft point and the pointer tip point connected by a line.

Because the cage axis has already been defined by acquiring three points before, restrictions are used to define such axis from pointer tip point to shaft point around the cage:

A distance between the pointer tip point and the cage tip point must be bigger than a predefined value, in particular 3 mm.

A distance between the pointer tip point and the cage tip point must be bigger than a predefined value, in particular 5 mm.

If the acquired axis does not fulfil the aforementioned restrictions, the acquired axis is discarded.

Thus, the user does not get a wrong axis, for example from erroneously holding still the pointer tip near the cage end.

According to another exemplary embodiment of the present invention, determining the virtual model of the cage comprises the steps of receiving a basic shape of the cage and determining the virtual model of the cage using basic shape of the cage.

Although an additional user input is not necessary for the method to approximate the shape of the cage to determine the virtual model, in some cases a user input providing additional shape information allows for a more precise approximation of the shape of the cage. Preferably, the user is provided with a graphic user interface for inputting the basic cage, for example by verifying one of a plurality of preselected shapes of the cages.

For example, the user inputs an ellipsoid, a lordotic shape, a bullet shape or a curved shape as a basic shape. For each basic shape, additional specific shape information may be provided by the user, for example a lordotic angle.

According to another exemplary embodiment of the present invention, the basic shape of the cage comprises an ellipsoid shape, a lordotic shape, a bullet shape, a round shape or a curve shape.

The following calculations are preferred according to the specific basic shapes:

Ellipsoid as Cage Shape:
While ellipses are defined by $$\left(\frac{x}{a}\right)^2 + \left(\frac{y}{b}\right)^2 = r^2$$

(for circles: a=b=1), a superellipse is a generalisation manipulating the 2-exponent:

$$\left(\frac{x}{a}\right)^s + \left(\frac{y}{b}\right)^s = r^s.$$

The parameter s is also called superness (D. Knuth) of the ellipse. Choosing s=∞ would lead to a rectangle, s=2 to an ellipse, s=1 to a rhombus, and s=∞ to a cross of infinitely thin lines.

Now one dimension is added towards an ellipsoid: using polar coordinates, let the rotation around azimuth angle (along the equator) describe a superellipse as above and the polar angle rotation another superellipse with superness t. This leads to a super-ellipsoid parametrized by radius on x-axis, radius on y-axis, radius on z-axis, azimuth superness s, and polar superness t. The parametric representation following spherical coordinates ν (polar angle or inclination from 0 to Pi) and φ (azimuthal angle from 0 to 2Pi) is $$x(\theta,\phi)=r_x \operatorname{sgn}(\sin\theta)|\sin\theta|^{2/t} \operatorname{sgn}(\cos\phi)|\cos\phi|^{2/s}$$

$$y(\theta,\phi)=r_y \operatorname{sgn}(\cos\theta)|\cos\theta|^{2/t} \operatorname{sgn}(\cos\phi)|\cos\phi|^{2/s}$$

$$z(\theta,\phi)=r_z \operatorname{sgn}(\sin\theta)|\sin\theta|^{2/t}$$

For triangulation, the resolution of the ellipsoid's surface triangles is defined as number n of equidistant angular subdivisions of the polar half circle for triangulation purpose. The equatorial circle is subdivided two times n, implicitly. For example setting n=2 and both supernesses to 1 would create an octahedron. To create a cage shape, instead higher superness and higher number n of subdivisions for smooth display is used, but n is limited due to performance reasons.

These ellipsoid coordinates are finally mapped to cage coordinates by a simple translation of the ellipsoid origin onto the cage centre meaning a translation by vector $(0,0,r_z)$, while the vectors of the ellipsoid coordinate system axes are identical to the vectors of the cage coordinate system, so the poles of the ellipsoid's spherical coordinates are located at cage start point S and cage end point E. Thus $r_z=0.5\|S-E\|_2$ while the calculation of $r_x$ and $r_y$ is described later on.

Lordotic Shape as Cage Shape:
The super-ellipsoid can be easily morphed into a lordotic cage with angle β by applying a linear transformation, for example on the ellipsoid's x coordinates in order to create an angle on a y-z-plane (cage left side and right side) along the ellipsoid's y coordinates as follows:

$$x'(\theta, \phi) = x(\theta, \phi)\left(1 + \frac{y\tan\beta}{r_x}\right)$$

Generally, each of the six "sides" of the cage (front, back, top, bottom, left, right) has two possibilities to get an angle, so x coordinates can be transformed along y-axis or z-axis while y coordinates can be transformed along x-axis or z-axis. Z-coordinates can be transformed along x-axis or y-axis though there is less benefit of creating an angle on the front and back "side" of the cage.

Bullet Shape as Cage Shape:

One typical cage shape is a so-called "bullet shape". There are several ways to create such a kind of shape.

Towards the "conical" side, the super-ellipsoid can be transformed into a conical or pyramidal shape for example by projecting the ellipsoid surface along the vector from ellipsoid surface to cage axis (in z-plane) onto a cone or 4-sided pyramid and linearly interpolating x and y-values from ellipsoid to the target shape near the tip of the cage.

Another approach is to change the superness parameters t of the super-ellipsoid, because (rounded) pyramid and cone are just special values of the superness parameters. For example, the polar superness parameter can be modified near the start point of the cage by generalizing it to a function $t(\theta)$, for example a step function or even better for instance an arcus tangent function for a soft change from one shape into another.

The polar angle has to be translated to the specific polar angle $\theta_{step}$ where the shape is changed and it has to be scaled so the step is not too hard, not too soft. The arcus tangent function is used to create the "soft" step and its output value also has to be translated and scaled, so the shapes for $t=t_0$ to $t=t_1$ are created.

Thus creating a "soft" step at $\theta_{step}$ from $t=t_0$ to $t=t_1$ can be performed as follows (where the softness of the step is S, e.g. S=0.2):

$$t(\theta) = t_0 + (t_1 - t_0)(-1)\left(\mathrm{atan}\left(\frac{1}{S}(\theta - \theta_{step})\right) + \frac{\pi}{2}\right)/\pi$$

Curved Shape as Cage Shape:

To create the curved shape of so-called kidney cages or "banana cages", a simple idea is to transform one coordinate axis, for example use a quadratic function f(z) on the z values along the cage axis:

$$y'(\theta,\phi) = y(\theta,\phi) f(z)$$

However, with higher cage bending b, the cage looks wider in the centre and narrower at start and end point.

Thus, it is essential to map the ellipsoid onto a torus ring with smaller inner radius and larger outer radius. Let r be the average of inner and outer radius of the torus, having cage tip point S and cage end point E and two nearest points N1 and N2 from the "parallel" lines, the box as shown below is transformed onto the ring as follows:

If the cage is bent into y-direction (x-direction is analogue) and the z-axis points from S to E, the general parametric representation of circle coordinates for a variable angle Y and radius R is $y = R\sin(Y)$ $z = R\cos(Y)$ Now the approach is to calculate the angle $2\alpha$ between lines S to centre of the ring and E to centre of the ring and map the z-values to angles. Furthermore, the y-values are directly mapped to the circle radius.

$$Y = \frac{\pi}{2} + \alpha \frac{-z}{r_z}$$

$$R = y + r$$

and the circle has to be translated back along y. Thus the ellipsoid to torus mapping is $$y''(\theta, \phi) = \sin\left(\frac{\pi}{2} - z(\theta, \phi)\frac{\alpha}{r_z}\right)(y(\theta, \phi) + r) - (r - b)$$

$$z''(\theta, \phi) = \cos\left(\frac{\pi}{2} - z(\theta, \phi)\frac{\alpha}{r_z}\right)(y(\theta, \phi) + r)$$

The formulas can be easily adjusted for x and negative b. They produce a bent ellipsoid mapped onto a torus ring.

Still the midline torus ring radius r (distance from S to C, which is the center of the torus ring, or distance from E to C) and the bending b of the cage, measured perpendicular to the cage axis, have to be determined.

A good approximation of the cage bending b can be calculated by projecting the two points N1 and N2 along the y-axis onto the cage axis, because the curvature of the circle is almost the same near the cage centre, independent of $\alpha$. Therefore the quotient of b', where b' is the bending at a quarter of the cage axis from S to E, and b can be approximated.

$$\cos\alpha \approx 1 - \frac{\alpha^2}{2}$$

$$g(\alpha) = \frac{b'}{b} = \frac{\sin\left(90° - \frac{\alpha}{2}\right) - \sin(90° - \alpha)}{\sin(90°) - \sin(90° - \alpha)} =$$

$$\frac{\cos(\alpha) - \cos(2\alpha)}{1 - \cos(2\alpha)} \approx \frac{1 - \frac{\alpha^2}{2} - \left(1 - \frac{4\alpha^2}{2}\right)}{1 - \left(1 - \frac{4\alpha^2}{2}\right)} = \frac{3}{4}$$

Even using a half circle, $$\frac{b'}{b} = \sin(45°) = 0.707,$$

so b will be a good approximation if extrapolated from the z coordinates of N1 and N2:

$$b_1 = \frac{1}{1 - \left(\frac{|z_{N_1} - r_z|}{r_z}\right)^2}$$

$$b_2 = \frac{1}{1 - \left(\frac{|z_{N_2} - r_z|}{r_z}\right)^2}$$

$$b = \frac{b_1 + b_2}{2}$$

Calculation of radius r:

The radius r of the torus ring is determined from a circle through points S, E and the centre point "bent" by value b. The circle equation is $$f(x) = \sqrt{1 - \left(\frac{x}{r}\right)^2} \cdot r - (r - b)$$

Now $f(r_x)=0$ has to be solved for radius r, resulting in:

$$r = \frac{b^2 - r_x^2}{2b}$$

According to another exemplary embodiment of the present invention, the method comprises the following steps: Receiving a diameter of the pointer shaft. Determining at least one corrected nearest point by shifting the at least one nearest point of the at least one axis towards the length cage axis or the width cage axis for half of the received diameter of the pointer shaft. Determining at least one projection point, projecting the at least one corrected nearest point into an x-y-plane, defined by the x-axis and the y-axis.

The at least one axis is defined by the pointer tip point and the pointer shaft point. As the pointing device itself comes with a certain diameter, a displacement has to be taken into account, so the axis has to be shifted by the pointing device diameter. Therefore, axes are compared pairwise. If two axes are approximately parallel, meaning the angle between both axes is smaller than 45 degree, the cage "inside" and "outside" for the axes is detected. So, a correction vector towards the cage axes can be defined. For correction of the axes, the nearest point to the cage axis is determined and the diameter of the pointing device at the nearest point is known from its specification. Thus, a corrected nearest point towards the cage axes from the nearest point along the correction vector can be calculated.

According to the present disclosure, a cage calibration system is provided, comprising a holding device with a tracker, a pointing device with a tracker and a tracking device, configured for tracking the tracker arranged on the holding device and the pointing device, the instrument calibration system being configured for executing the method of calibrating a cage, as described herein.

According to the present disclosure, a surgical navigation system for computer assisted surgery is provided, the system comprising a cage calibration system, as described herein.

According to the present disclosure a computer program is provided, which, when running on a computer or when loaded onto a computer, causes the computer to perform the method steps of the method, as described herein. Further, a program storage medium is provided, on which the program is stored. Further, a computer is provided, comprising at least one processor and a memory and/or the program storage medium, wherein the program is running on the computer or loaded into the memory of the computer. Further, a signal wave or a digital signal wave is provided, carrying information which represents the program and/or a data stream which is representative of the program.

For example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

For example, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to calibration of a image-guided navigation system. For this reason alone, no surgical or therapeutic activity and in particular no surgical or therapeutic step is necessitated or implied by carrying out the invention.

DEFINITIONS

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Registering

The n-dimensional image of a body is registered when the spatial location of each point of an actual object within a space, for example a body part in an operating theatre, is assigned an image data point of an image (CT, MR, etc.) stored in a navigation system.

Image Registration

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Marker Device

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

Marker Holder

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

Pointer

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

Reference Star

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

Navigation System

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:

a computer for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Surgical Navigation System

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Referencing

Determining the position is referred to as referencing if it implies informing a navigation system of said position in a reference system of the navigation system.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein FIG. 1 schematically shows transformations and coordinate systems in a cage calibration system.

DESCRIPTION OF EMBODIMENTS

Figure 1:
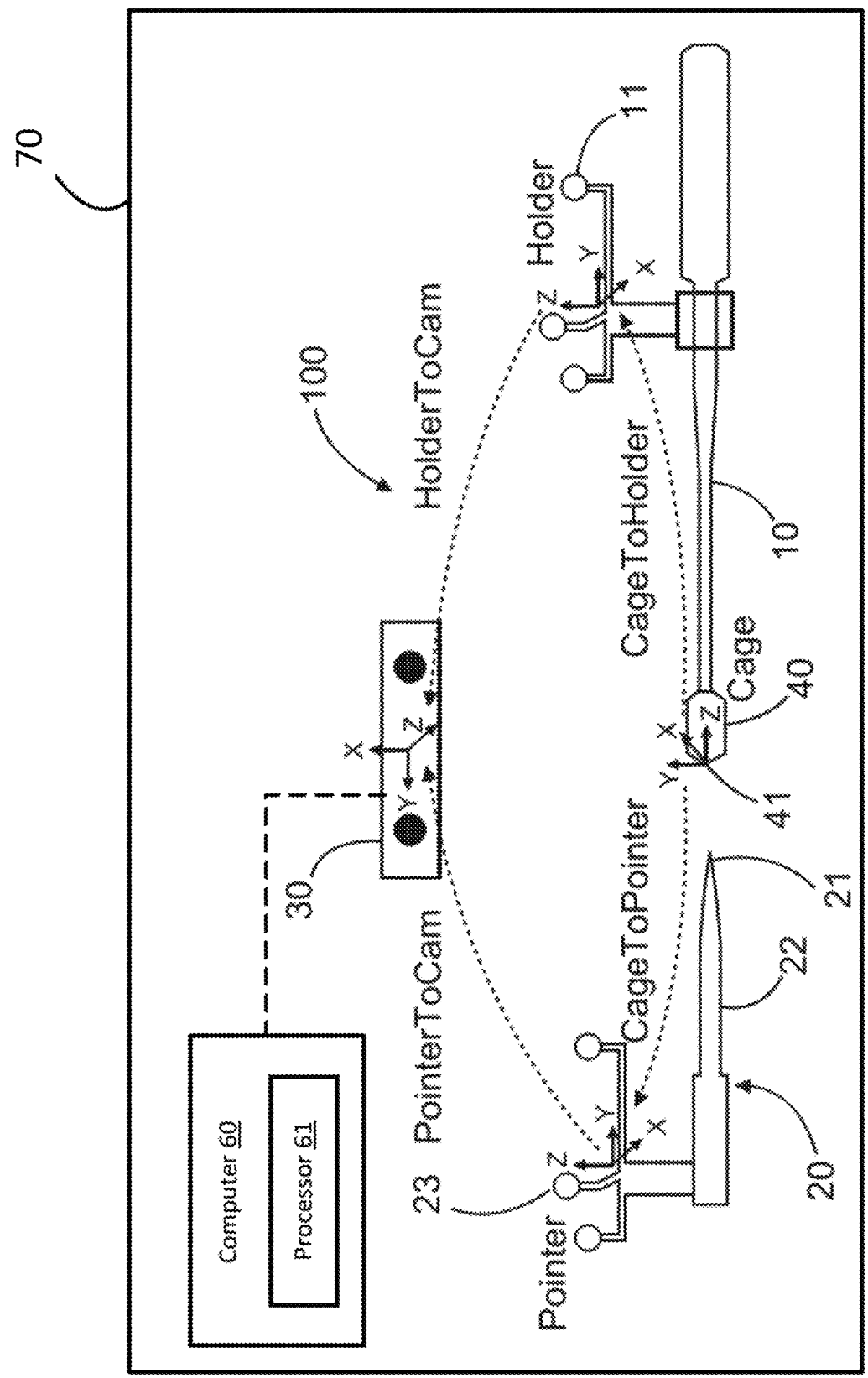

FIG. 1 describes a cage calibration system 100 for calibrating a first cage 40. The cage calibration system 100 comprises a tracking device 30, a pointing device 20 and a holding device 10. The tracking device 30 is configured for tracking objects, in particular for tracking markers disposed on the objects. In this case, the tracking device 30 is configured for tracking the holding device 10 by tracking a holding marker 11 disposed on the holding device 10 and for tracking the pointer device 20 by tracking a pointer marker 23 disposed on the pointer device 20. The holding marker 11 and the pointer marker 23 comprise a marker array of three infrared reflecting spheres. The tracking device 30 in this case is an infrared camera capable of detecting the pointer marker 23 and the holder marker 11 disposed at the pointing device 20 and the holding device 10, respectively.

The holder marker 11 defines a holder coordinate system Holder and the pointer marker 23 defines a pointer coordinate system Pointer. The tracking device 30 defines a camera coordinate system Cam.

For tracking the holder 10, the tracking device 30 tracks the holder marker 11. However, without calibrating the first cage 40, the navigation system 70 (which includes, for example, a computer 60 having a processor 61) using the input of the tracking device 30 is not aware of the shape, position or orientation of the first cage 40. The navigation system 70 however is provided with the shape, position and orientation of the pointer device 20, which can be tracked using the tracking device 30 over the pointer marker 23. For calibrating the first cage 40, the pointer device 20 is held against the first cage 40 for determining different points of the first cage 40. The first cage 40 defines a cage coordinate system Cage, which is preferably set at a cage tip 41 of the first cage 40. In other words, the calibration comprises determining a transformation from the cage coordinate system Cage to other coordinate systems, in particular a cage-to-holder-coordinate-transformation CageToHolder, which describes a transformation between the holder coordinate system Holder of the holding device 10 and the cage coordinate system Cage of the first cage 40. In other words, a relationship between the different coordinate systems is determined for calibrating the first cage 40.

All transformations are invertible, so for example, if the cage-to-holder-coordinate-transformation CageToHolder is known, consequently the holder-to-cage-coordinate-transformation HolderToCage is known. Consequently, those invertible notations are also used.

The transformations define how the coordinates of one system transform into coordinates of another system. After getting the positions of the markers 11, 23 from the tracking device 30, an algorithm assigns the markers 11, 23, so the markers 11, 23 are identified and a coordinate system can be clearly defined for each marker array 11, 23. The marker positions of the marker array given by the tracking system 30 are matched (e.g. "Kabsch algorithm") to expected positions of the marker array.

Due to the pointer marker 23 and the holder marker 11, a pointer-to-cam-coordinate-transformation PointerToCam and a holder-to-cam-coordinate-transformation HolderToCam can be easily determined. With the help of the pointing device 20, the cage-to-holder-coordinate-transformation CageToHolder is determined. This is possible, as a cage-to-pointer-coordinate-transformation CageToPointer can be determined by holding the pointing device 20 at different points on the cage 40.

The pointer device 20 comprises a pointer tip 21 and a pointer shaft 22. When holding the pointer tip 21 against the first cage 40, a single point of the first cage 40 can be acquired. However, when holding the pointer shaft 22 against the first cage 40, a whole axis, or in other words a plurality of points of the first cage 40 can be acquired.

In the following figures, different cages and virtual models of those cages are described. However, although some elements of those cages differ in particular in their position due to different shapes of the cages, those elements are indicated with the same reference sign throughout the figures. Those elements comprise in particular a cage tip point S, a cage end point E, a length cage axis Al, a width length axis Aw, a first lateral side sl1, a second lateral side l2, a top side st and a bottom side sb.

Figure 2:
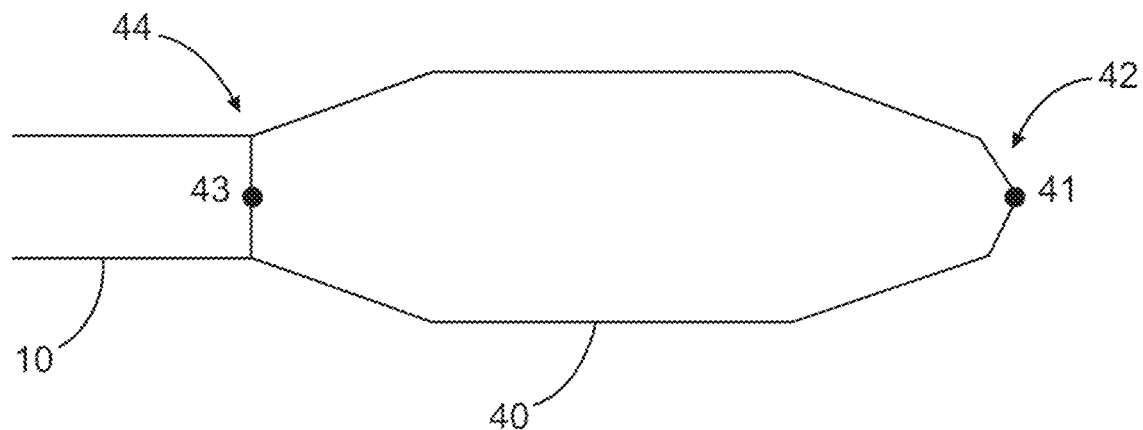
FIG. 2 shows a schematic view of a first cage according to a first embodiment.

FIG. 2 describes a schematic view of the first cage 40. The first cage 40 comprises a front side 42 and an end side 44, which is disposed opposite to the front side 42. The first cage 40 is held by the holding device 10 at the end side 44 of the first cage 40. At the end side 44, the first cage 40 comprises a first cage end 43. The first cage 40 comprises a first cage tip 41 at the front side 42. The first cage tip 41 and the first cage end 43 are crucial points for calibrating the first cage 40.

Figure 3:
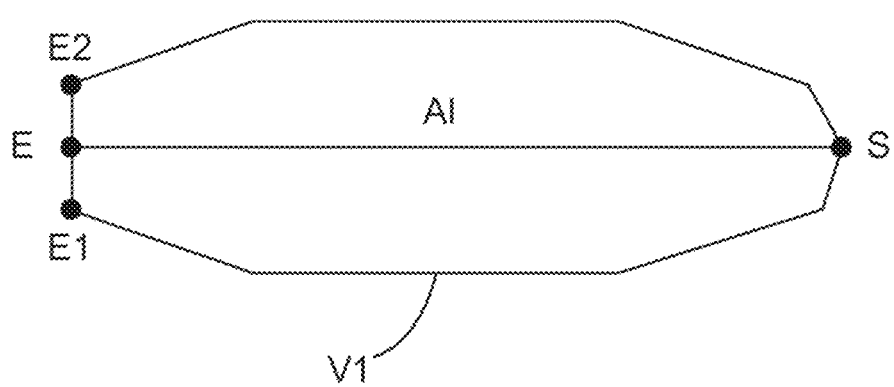
FIG. 3 shows a schematic view of a first virtual model of a first cage of the first embodiment.

FIG. 3 describes a schematic view of a first virtual model V1 of the first cage 40, determined by calibrating the first cage 40. By holding the pointer tip 21 of the pointing device 20 against the first cage tip 41, a cage tip point S can be acquired. The holding device 10 however makes the first cage end 43 inaccessible for the pointing device 20. Consequently, the pointer tip 21 is held against lateral sides of the cage holder 10, where the cage holder 10 connects with the first cage 40. Thus, a first holder point E1 and a second holder point E2 can be acquired. A cage end point E relating to the first cage end 43 is thus acquired by determining the centre of a line connecting the first holder point E1 and the second holder point E2.

A cage axis, in this case a length cage axis Al, is determined by connecting the cage end point E with the cage tip point S. The length cage axis Al is the most simple representation, in other words virtual model, of the first cage 40.

Figure 4:
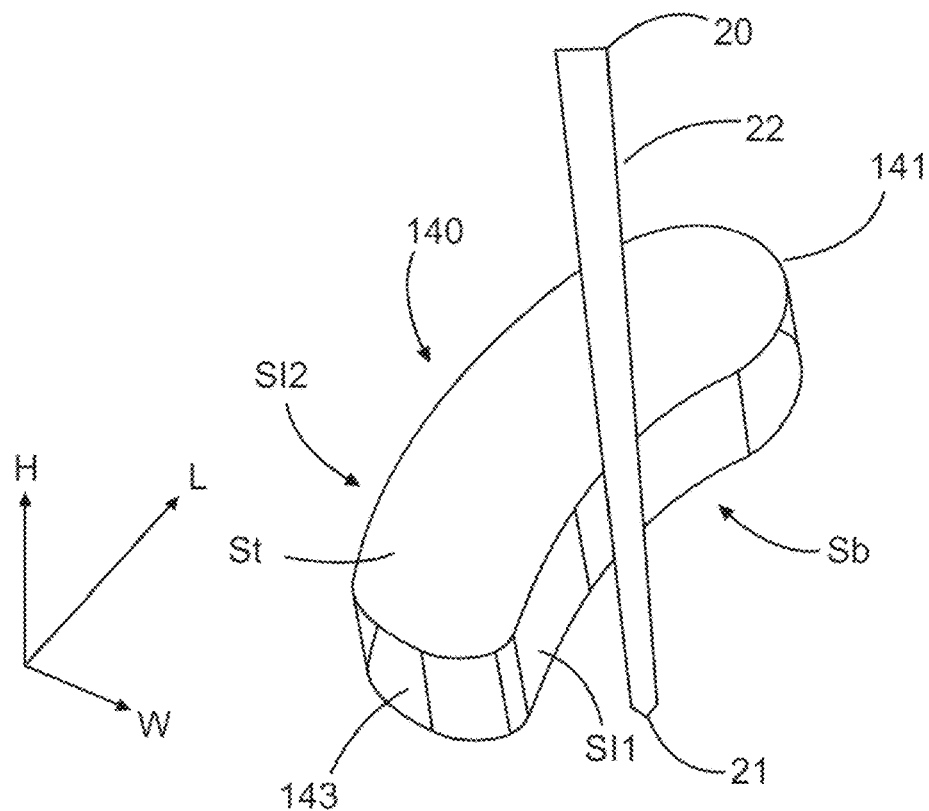
FIG. 4 is a perspective view of a second cage according to a second embodiment with a pointing device at one position.

FIG. 4 describes a perspective view of the second cage 140 according to a second embodiment, with a second cage tip 141 and a second cage end 143. The second cage 140 has a basic shape of a kidney or "banana" with a constant height in a height direction H. The length of the second cage 140 extends in a length direction L from the second cage tip 141 to the second cage end 143. Consequently, the second cage 140 has a width in a width direction W. The second cage 140 further comprises a first lateral side sl1 and a second lateral side sl2. The second cage 140 further comprises a top side st and a bottom side sb. FIG. 4 indicates the pointing device 20. In fact, FIG. 4 indicates the pointer tip 21 and the pointer shaft of the pointing device 20. In order to determine a more detailed virtual model of the second cage 140, the pointer shaft 20 is held against the first lateral side sl1 to acquire an axis of the second cage 140. Using the acquired axis, together with holding the pointer tip 21 against the second cage end 143 and the second cage tip 141 as described above, a more detailed virtual model of the second cage 140 can be determined.

Figure 5:
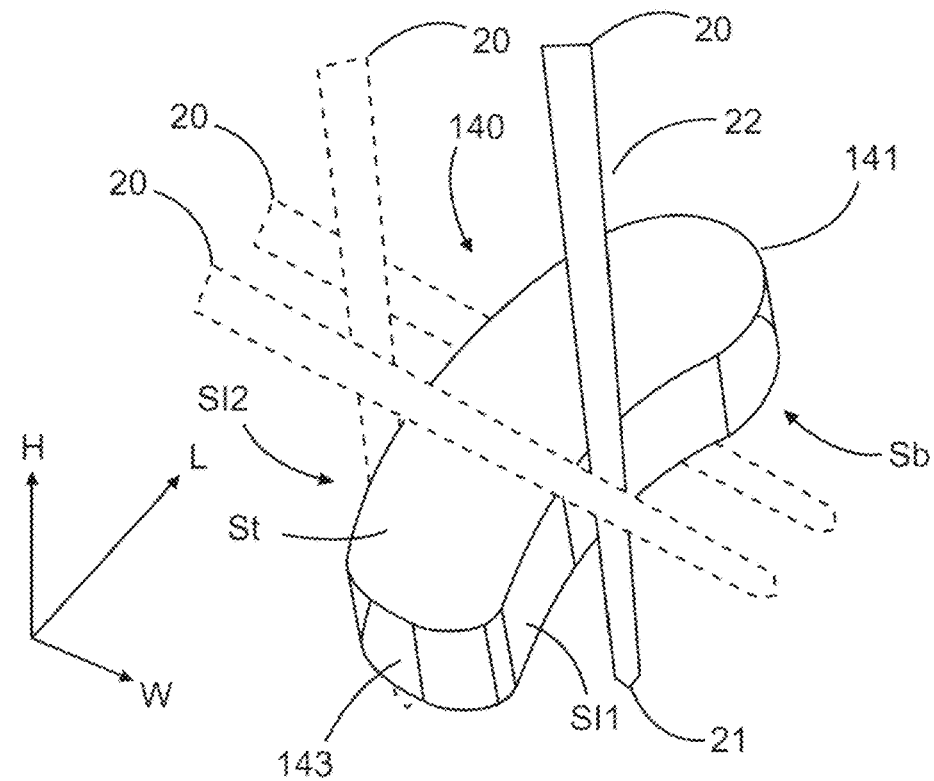
FIG. 5 is a perspective view of the second cage of the second embodiment with a pointing device indicated at different positions.

FIG. 5 describes the perspective view of a cage of FIG. 4 with the pointing device 20 being indicated at different positions. In order to achieve a good 3D estimate virtual model of the second cage 140, four axes are acquired. This is executed by holding the pointer shaft 21 against the first lateral side sl1 in the height direction, against the second lateral side sl2 in the height direction, against the top side st in the width direction and against the bottom side sb in the width direction. In should be noted that FIG. 5 does not indicate four pointing devices 20, but only one pointing device 20 that is disposed at four different positions after another to acquire the four axes X1, X2, X3, X4.

Figure 6:
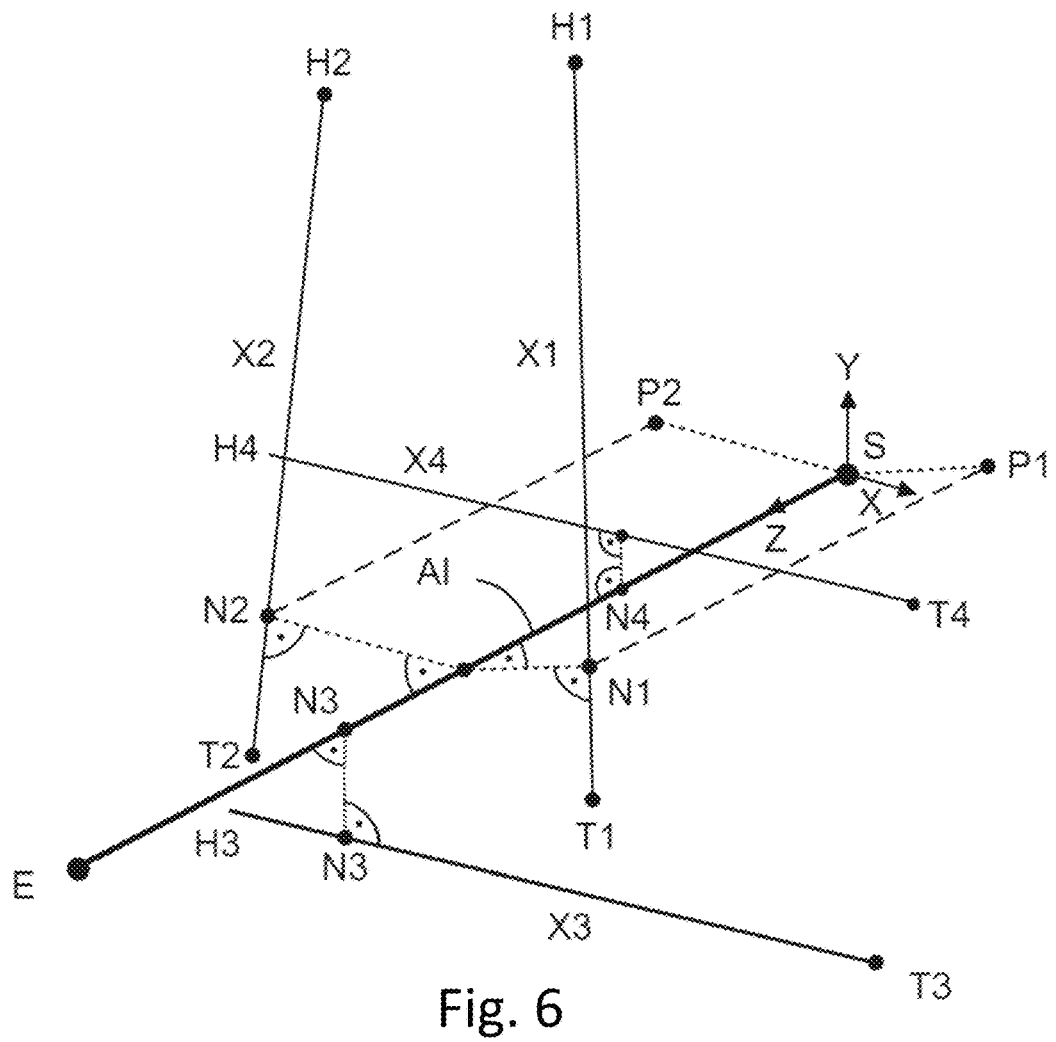
FIG. 6 schematically shows a plurality of acquired axes of the second cage.

FIG. 6 schematically shows the plurality of acquired axes X1, X2, X3, X4, namely the first axis X1 relating to the first lateral side sl1, the second axis X2 relating to the second lateral side sl2, the third axis X3 relating to the bottom side sb and the fourth lateral side relating to the top side st. In addition, FIG. 6 shows a cage tip point S relating to the second cage tip 141 and an end point E relating to the second cage end 143. The cage axis, in this case the length cage axis Al, is determined by a connection between the cage tip point S and the end point E. At the cage tip point S, the cage coordinate system Cage is disposed. The cage coordinate system comprises an x-axis, a y-axis and a z-axis, perpendicular to each other, wherein the z-axis runs along the length cage axis Al.

For each axis, X1, X2, X3, X4 a nearest point N1, N2, N3, N4, being the nearest point of the axis X1, X2, X3, X4 to the length cage axis Al is determined. The nearest points N1, N2, N3, N4 are determined by a connection between the respective axis X1, X2, X3, X4 to the length cage axis Al being perpendicular to the length cage axis Al and the respective axis X1, X2, X3, X4.

Furthermore, FIG. 6 shows a first projection point P1, being the projection along the Z-axis of the cage coordinate system Cage of the first nearest point N1 into the X-Y plane of the cage coordinate system Cage. Also a second projection point P2 is shown, being the projection along the Z-axis of the cage coordinate system Cage of the second nearest point N2 into the X-Y-plane of the cage coordinate system Cage.

The first projection point P1 and the second projection point P2 are used in a function, deciding of the acquired first axis X1 and/or the acquired second axis X2 are newly introduced axes or new measurements of an already planned axis.

The acquired axes X1, X2, X3, X4 are determined by acquiring a plurality of points along the respective axes X1, X2, X3, X4. In this case, the first axis X1 is defined by an acquired first shaft point H1 and by an acquired first pointer tip point T1. The second axis X2 is defined by an acquired second shaft point H2 and by an acquired second pointer tip point T2. The third axis X3 is defined by an acquired third shaft point H3 and by an acquired third pointer tip point T3. The fourth axis X4 is defined by an acquired fourth shaft point H4 and by an acquired fourth pointer tip point T4. The shaft points H1, H2, H3, H4 relate to an end of the pointer shaft 22 distant to the pointer tip 21, when holding the pointing device 20 in the respective position of acquiring the respective axis X1, X2, X3, X4. The pointer tip points T1, T2, T3, T4 relate to the pointer tip 21, when holding the pointing device 20 in the respective position of acquiring the respective axis X1, X2, X3, X4.

Based on the acquired axes X1, X2, X3, X4, the cage tip point S and the cage end point E, a bounding box can be determined approximating a virtual model of the cage 40 that also is calibrated.

Figure 7:
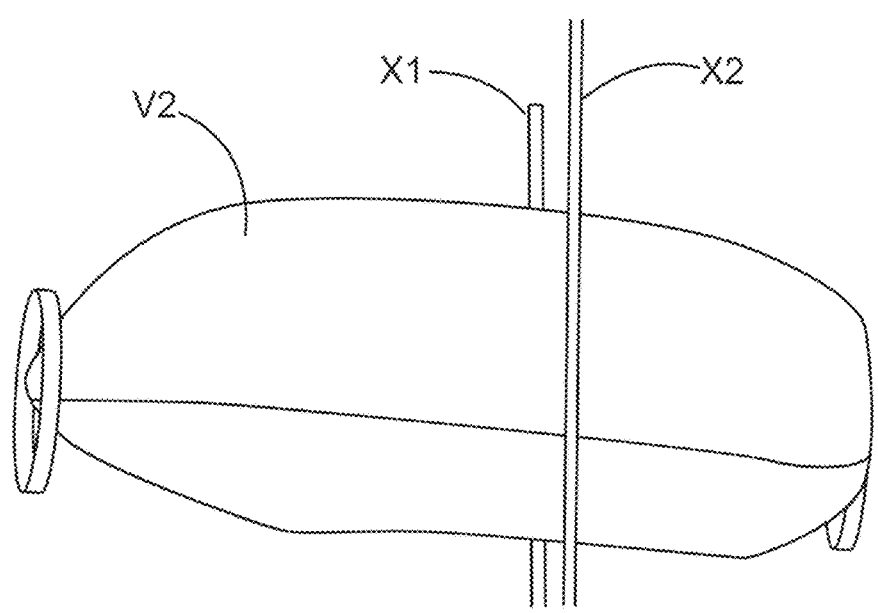
FIG. 7 schematically shows a second virtual model of the second cage.

FIG. 7 schematically shows a second virtual model V2 of the second cage 140, as it is determined based on the acquired axes X1, X2, X3, X4, the cage tip point S and the end point E. For comparison, the acquired axes X1 and X2 are also indicated next to the second virtual model V2.

Figure 8:
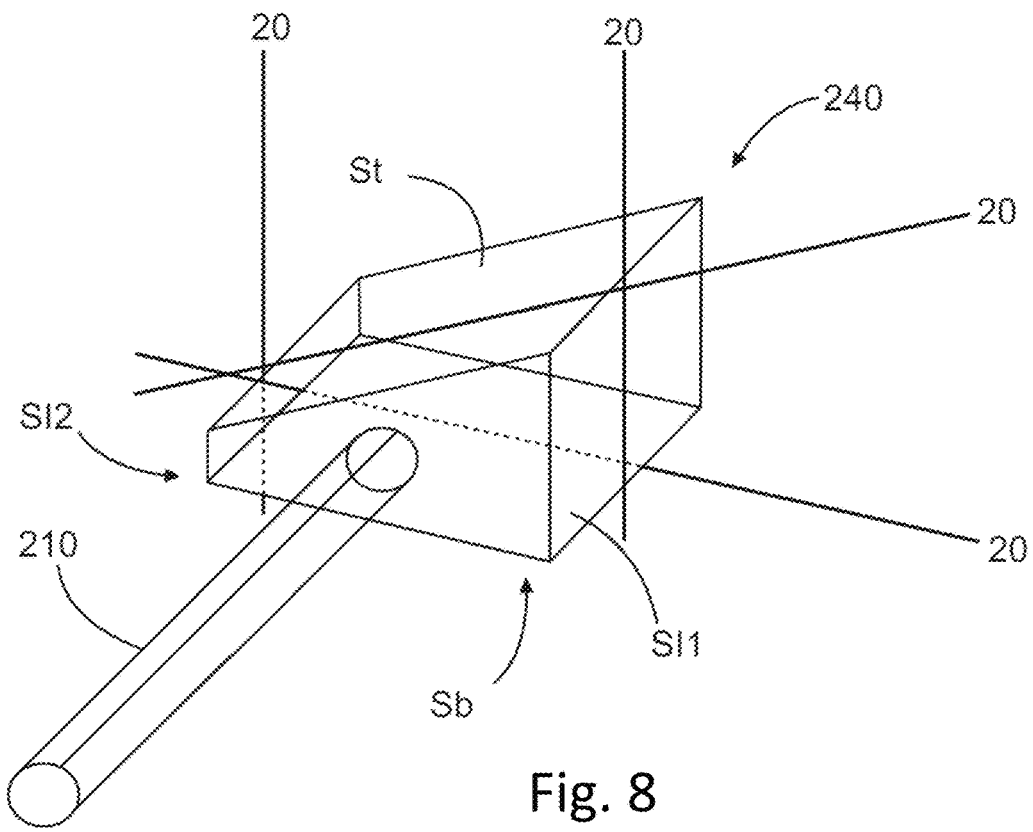
FIG. 8 schematically shows a third cage according to a third embodiment.

FIG. 8 schematically shows a third cage 240 according to a third embodiment. The third cage 240 comprises a top side st that is inclined in the width direction W. In addition, the third cage 240 comprises a first lateral side sl1 and a second lateral side sl2, as well as a bottom side sb. For each acquired side, a position of the pointing device 20 held against the respective side st, sl1, sl2, sb is indicated. The third cage 240 is held by a second holding device 210.

Figure 9:
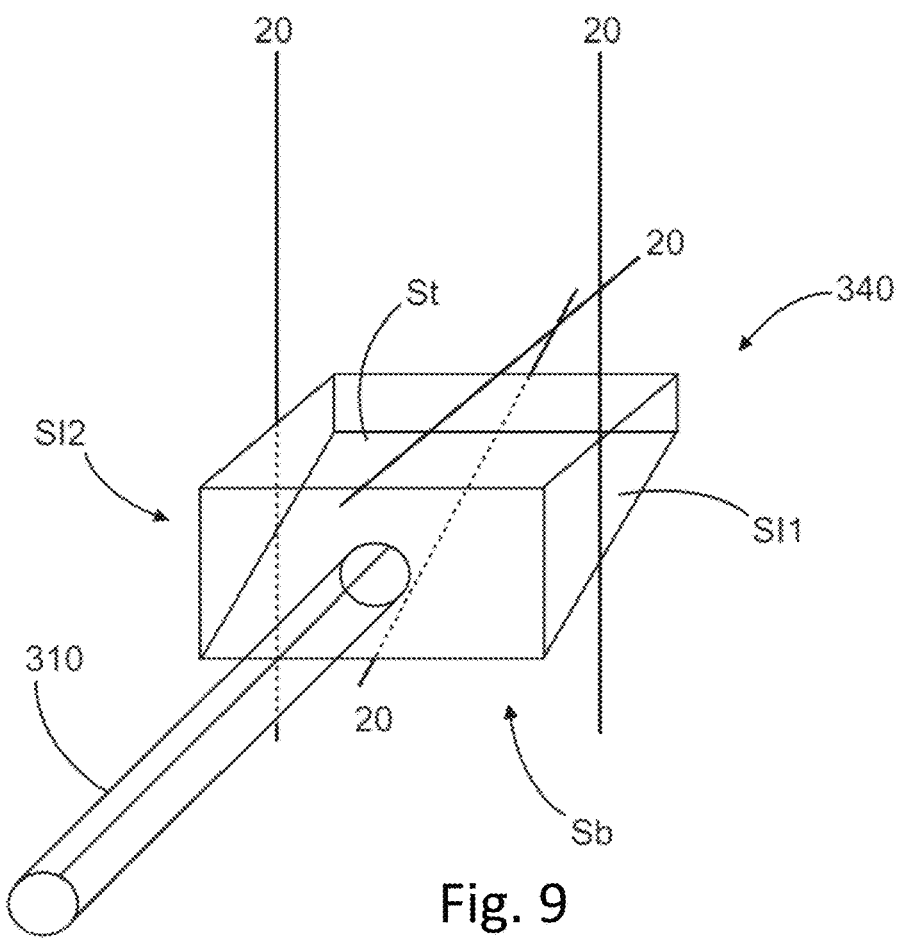
FIG. 9 schematically shows a fourth cage according to a fourth embodiment.

FIG. 9 schematically shows a fourth cage 340 according to a fourth embodiment. The fourth cage 340 comprises a top side st that is inclined in the length direction L. In addition, the fourth cage 340 comprises a first lateral side sl1 and a second lateral side sl2, as well as a bottom side sb. For each acquired side, a position of the pointing device 20 held against the respective side st, sl1, sl2, sb is indicated.

Figure 10:
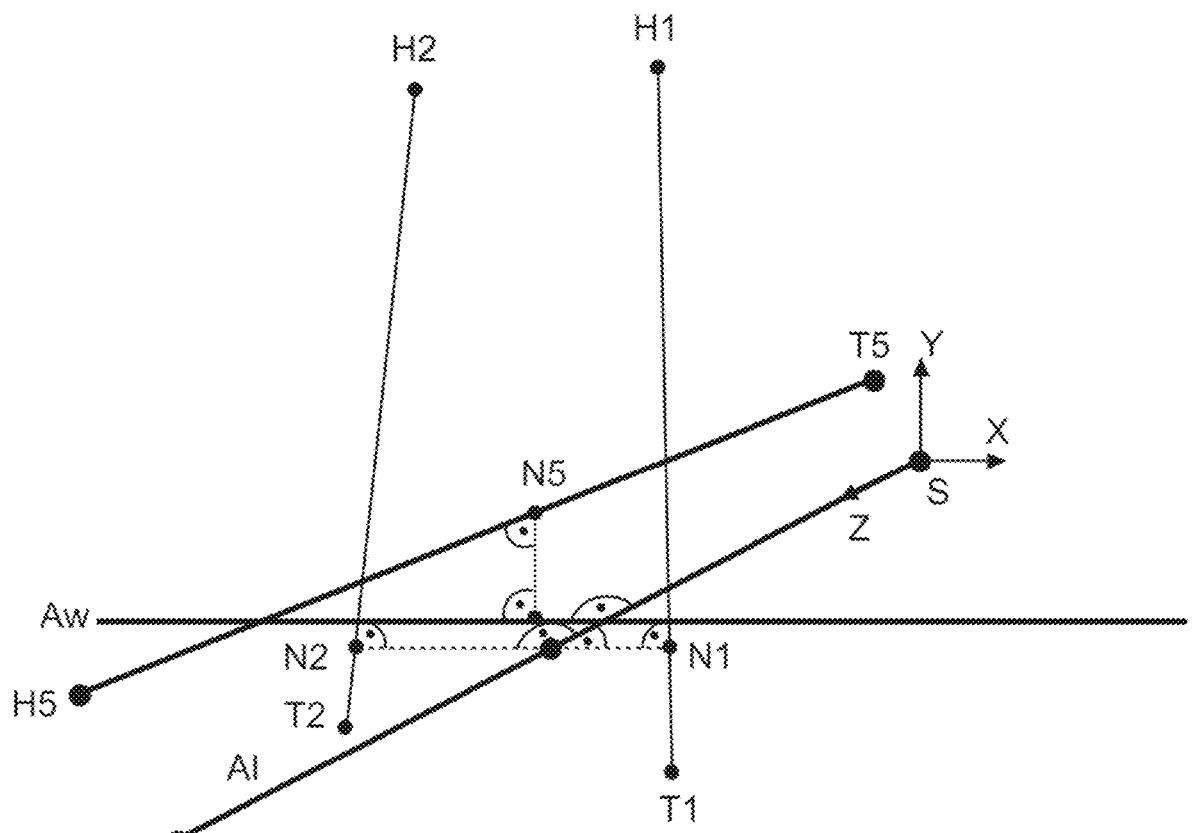
FIG. 10 schematically shows a plurality of acquired axis of the fourth cage.

FIG. 10 schematically shows a schematic view of acquired axis relating to the fourth cage 340. Compared to the third cage 240 of FIG. 8, instead of the fourth axis X4, a fifth axis X5 is acquired by holding the pointer shaft 21 against the top side st in the length direction L. Consequently, when determining a fifth nearest point N5, the reference axis is not the length cage axis Al, but a width cage axis Aw extending in the width direction W, being perpendicular to a length cage axis Al.

Figure 11:
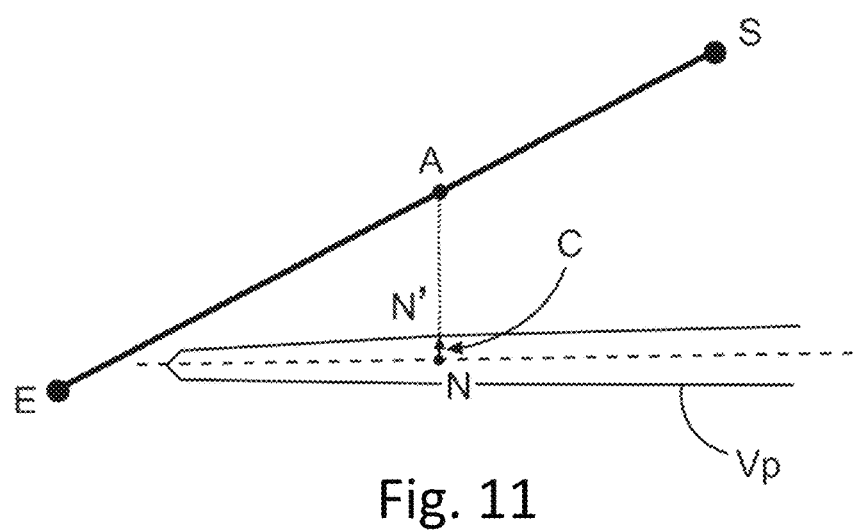
FIG. 11 schematically shows the consideration of the diameter of pointing device.

FIG. 11 schematically shows the consideration of a diameter of the pointing device 20. In FIG. 11, a pointing device model Vp, being a virtual model of the pointing device 20, is indicated. A nearest point N to the cage axis A is indicated. However, as the pointing device 20 has a certain diameter, an error is introduced that can be omitted, as the shape of the pointing device 20 is already known. Thus, a correction vector C is determined extending from the nearest point N towards the cage axis A. The correction vector C has a length equal to the diameter of the pointing device 20 in the nearest point N. Thus, a corrected nearest point N' is determined by applying the correction vector C to the corrected nearest point N'.

Figure 12:
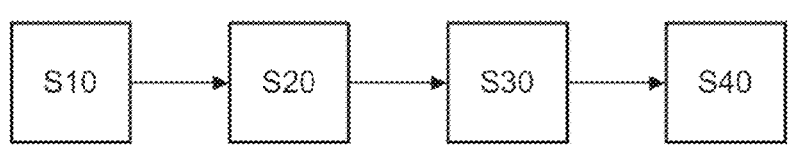
FIG. 12 schematically shows the cage calibration method.

FIG. 12 schematically shows the cage calibration method. In a first step S10 by using a pointer tip 21 of a pointing device 20, a cage tip point S is acquired at a cage tip 41 of the cage 40, wherein the cage tip is disposed at a first end 42 of the cage in a length direction L of the cage. In a second step S20, by using the pointer tip 21 of the pointing device 20, a cage end point E is acquired at a cage end 43 of the cage 40, wherein the cage end 43 is disposed at a second end 44 of the cage 40, opposing to the first end 42, in the length direction L. In a third step S30, by using a pointer shaft 22 of the pointing device 20, at least one axis X1, X2, X3, X4 along a side Sl1, Sl2, St, Sb of the cage 40 is acquired. In a fourth step S40, a calibrated virtual model V1, V2 of the cage 40 is determined using the cage tip point S, the cage end point E and the at least one cage axis X1, X2, X3, X4.

The invention claimed is:

1. A computer implemented medical method of calibrating a cage, comprising the steps:
   acquiring, by holding a pointer tip of a pointing device against a cage tip of the cage, a cage tip coordinate at the cage tip of the cage, wherein the cage tip is disposed at a first end of the cage in a length direction of the cage;
   acquiring, by holding the pointer tip of the pointing device against a cage end of the cage, a cage end coordinate at the cage end of the cage, wherein the cage end is disposed at a second end of the cage, opposing to the first end, in the length direction;
   acquiring, by holding a pointer shaft of the pointing device against a cage side of the cage, at least one axis along the side of the cage, wherein the pointer shaft relates to a part of the pointing device, extending away from the pointer tip; and
   determining a calibrated virtual model of the cage using the cage tip coordinate, the cage end coordinate and at least one cage axis.

2. The method of claim 1,
   wherein acquiring the cage end coordinate, the cage tip coordinate and/or the at least one cage axis comprises:
   determining a cage-to-holder-coordinate-transformation (CageToHolder), which describes a transformation between a holder coordinate system (Holder) of a holding device and a cage coordinate system of the cage.

3. The method of claim 2,
   wherein acquiring the cage end coordinate, the cage tip coordinate and/or the at least one axis comprises providing a pointer-to-holder-coordinate-transformation (PointerToHolder), which describes a transformation between the pointer coordinate system (Pointer) and the holder coordinate system (Holder); and
   determining a holder-to-cage-coordinate-transformation (HolderToCage), by using the pointer-to-holder-coordinate-transformation (PointerToHolder).

4. The method of claim 1,
   wherein acquiring the cage end coordinate, the cage tip coordinate and/or the at least one axis comprises holding the pointing device onto the cage until the respective cage end coordinate, cage tip coordinate and/or at least one axis is acquired.

5. The method of claim 1,
   wherein the virtual model indicates a shape, position and orientation of the cage.

6. The method of claim 1,
   wherein the virtual model comprises a multi-dimensional representation of the cage, in particular a 3-dimensional representation of the cage.

7. The method of claim 1,
   wherein acquiring the cage end coordinate comprises:
   acquiring a first holder point and a second holder point at opposing lateral sides of a cage holder, which holds the cage at the second end of the cage, by using the pointer tip of the pointing device; and
   determining the cage end coordinate as a centre of a connection line between the first holder point and the second holder point.

8. The method of claim 1, comprising the step:
   acquiring, by using the pointer shaft of the pointing device, at least one axis along at least one lateral side of the cage in a height direction of the cage.

9. The method of claim 8, comprising the step:
   acquiring, by using the pointer shaft of the pointing device, at least one axis along a top side and/or bottom side of the cage in a width direction of the cage.

10. The method of claim 8, comprising the step:
    acquiring, by using the pointer shaft of the pointing device, at least one axis along a top side and/or bottom side of the cage in a length direction of the cage.

11. The method of claim 1, comprising the steps:
    acquiring, by using the pointer shaft of the pointing device,
    a first axis along a first lateral side of the cage in a height direction of the cage;
    a second axis along a second lateral side of the cage opposite of the first lateral side, in the height direction of the cage;
    a third axis along a top side of the cage in a width direction of the cage; and
    a fourth axis along a bottom side of the cage in the width direction of the cage.

12. The method of claim 1, comprising the steps:
    acquiring, by using the pointer shaft of the pointing device,
    a first axis along a first lateral side of the cage in a height direction of the cage;
    a second axis along a second lateral side of the cage opposite of the first lateral side, in the height direction of the cage;
    a fifth axis along a top side of the cage in a length direction of the cage; and
    a sixth axis along a bottom side of the cage in the length direction of the cage.

13. The method of claim 1,
    wherein, for acquiring the at least one axis in a width direction and/or height direction, the pointer shaft is held in a width axis section distant to the cage end coordinate and the cage tip coordinate.

14. The method of claim 1,
    wherein, for acquiring the at least one axis in the length direction, the pointer shaft is held in a length axis section distant to the lateral sides of the cage.

15. The method of claim 1,
    wherein determining a calibrated virtual model comprises:
    determining a cage axis of the cage;
    determining at least one nearest point of the at least one axis, being the nearest point of the at least one axis to the cage axis; and
    determining the virtual model using the at least one nearest point.

16. The method of claim 15,
    wherein determining the at least one nearest point comprises:

determining a length cage axis connecting the cage tip coordinate and the cage end coordinate;

determining a width cage axis, extending perpendicular to the length cage axis in a width direction through a centre of the length cage axis in the length direction;

determining at least one nearest point of the at least one axis in the width direction and/or a height direction, being the nearest point of the at least one axis to the length cage axis; and determining at least one nearest point of the at least one axis in the length direction being the nearest point of the at least one axis to the width cage axis.

17. The method of claim 15, comprising the steps:

determining the cage coordinate system in the cage tip point coordinate, wherein the cage coordinate system comprises an x-axis, a y-axis and a z-axis, perpendicular to each other, wherein the z-axis is equal to the cage axis;

determining at least one projection point, projecting the at least one nearest point into an x-y-plane, defined by the x-axis and the y-axis;

determining a distance between the at least one projection point and an at least one planned projection point of a planned axis, wherein the at least one planned axis is a previously acquired axis for the cage;

replacing the planned axis with the acquired at least one axis; if the determined distance is smaller than a predetermined threshold; and adding the acquired at least one axis to the previously acquired axis for the cage.

18. The method of claim 17, wherein replacing the planned axis with the acquired at least one axis comprises:

determining a replacement likelihood score for each planned axis;

replacing the planned axis with the highest replacement likelihood score with the acquired at least one axis; and wherein the replacement likelihood score is determined using a weighted replacement likelihood function, using a distance of the planned axis to the cage axis and a distance of the planned axis to the acquired axis.

19. The method of claim 1, wherein determining the at least one axis comprises:

acquiring at least one shaft point relating to a shaft end distant to the pointer tip and at least one pointer tip point; and determining the at least one axis by connecting the at least one shaft point and the at least one pointer tip point.

20. The method of claim 1, wherein determining the virtual model of the cage comprises:

receiving a basic shape of the cage; and determining the virtual model of the cage using the basic shape of the cage.

21. The method of claim 19, wherein the basic shape of the cage comprises an ellipsoid shape, a lordotic shape, a bullet shape, a round shape or a curve shape.

22. The method of claim 1, comprising the steps:

receiving a diameter of the pointer shaft;

determining at least one corrected nearest point by shifting the at least one nearest point of the at least one axis towards the cage axis for half of the received diameter of the pointer shaft; and determining at least one projection point, projecting the at least one corrected nearest point into an x-y-plane, defined by the x-axis and the y-axis.

23. A cage calibration system comprising a processor configured to calibrate a cage, wherein the processor is programmed to perform operations of:

acquiring, by using a pointer tip of a pointing device, a cage tip coordinate at a cage tip of the cage, wherein the cage tip is disposed at a first end of the cage in a length direction of the cage;

acquiring, by using the pointer tip of the pointing device, a cage end coordinate at a cage end of the cage, wherein the cage end is disposed at a second end of the cage, opposing to the first end, in the length direction;

acquiring, by using a pointer shaft of the pointing device, at least one axis along a side of the cage;

determining a calibrated virtual model of the cage using the cage tip coordinate, the cage end coordinate and at least one cage axis;

a holding device with a holding device tracker;

the pointing device with a pointing device tracker; and a tracking device, configured for tracking the holding device tracker arranged on the holding device and the pointing device tracker.

24. A surgical navigation system for computer assisted surgery, the surgical navigation system including the cage calibration system according to claim 23.

25. A computer implemented method which, when executed by at least one processor on at least one computer, causes the at least one processor to:

acquire, by using a pointer tip of a pointing device, a cage tip coordinate at a cage tip of the cage, wherein the cage tip is disposed at a first end of the cage in a length direction of the cage;

acquire, by using the pointer tip of the pointing device, a cage end coordinate at a cage end of the cage, wherein the cage end is disposed at a second end of the cage, opposing to the first end, in the length direction;

acquire, by using a pointer shaft of the pointing device, at least one axis along a side of the cage; and determine a calibrated virtual model of the cage using the cage tip coordinate, the cage end coordinate and at least one cage axis.

* * * * *

UNITED STATES PATENT AND TRADEMARK OFFICE
CERTIFICATE OF CORRECTION

PATENT NO. : 12,076,093 B2
APPLICATION NO. : 17/599156
DATED : September 3, 2024
INVENTOR(S) : Thomas Drexl It is certified that error appears in the above-identified patent and that said Letters Patent is hereby corrected as shown below:

In the Specification

In Column 12, Line 27, delete "S=∞" and insert -- $s = 0$ --, therefor.

In Column 12, Line 36, delete "v" and insert -- $\theta$ --, therefor.

In the Claims

In Column 27, Claim 3, Line 50, delete "the" and insert -- a --, therefor.

In Column 29, Claim 17, Line 15, after "tip" delete "point".

Signed and Sealed this
Third Day of December, 2024

Katherine Kelly Vidal
*Director of the United States Patent and Trademark Office*